United States Patent
Rees et al.

(10) Patent No.: US 10,102,344 B2
(45) Date of Patent: Oct. 16, 2018

(54) SYSTEM AND METHODS FOR ANALYZING BLOOD GLUCOSE DATA AND QUANTIFYING THE SUCCESS OR FAILURE OF INSULIN THERAPY

(71) Applicant: Roche Diabetes Care, Inc., Indianapolis, IN (US)

(72) Inventors: Christen A Rees, Indianapolis, IN (US); Robin Wagner, Indianapolis, IN (US); Nathan Wegmann, St. Paul, MN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 597 days.

(21) Appl. No.: 13/803,770

(22) Filed: Mar. 14, 2013

(65) Prior Publication Data

US 2014/0278124 A1    Sep. 18, 2014

(51) Int. Cl.
| | | |
|---|---|---|
| G16H 50/30 | (2018.01) | |
| G06F 19/00 | (2018.01) | |
| A61B 5/145 | (2006.01) | |
| G01N 33/66 | (2006.01) | |
| A61B 5/00 | (2006.01) | |

(52) U.S. Cl.
CPC ...... *G06F 19/3431* (2013.01); *A61B 5/14532* (2013.01); *A61B 5/4833* (2013.01); *G01N 33/66* (2013.01); *G16H 50/30* (2018.01); *G01N 2800/042* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2009/0171589 A1 | 7/2009 | Kovatchev | |
| 2011/0021898 A1* | 1/2011 | Wei et al. | 600/365 |
| 2011/0237918 A1* | 9/2011 | Wagner et al. | 600/365 |
| 2012/0172694 A1 | 7/2012 | Desborough et al. | |

FOREIGN PATENT DOCUMENTS

WO    2014/009337 A1    1/2014

OTHER PUBLICATIONS

Kovatchev, "Symmetrization of the blood glucose measurement scale and its applications," Diabetes Care, vol. 20(11), p. 1655-1658, 1997.*
Kovatchev, Boris et al., "Assessment of Risk for Severe Hypoglycemia Among Adults with IDDM", Diabetes Care, vol. 21, No. 11, Nov. 1998, pp. 1870-1875.
Pitsillides, Achilleas et al., "Hypoglycemia Risk and Glucose Variability Indices Derived from Routine self-Monitoring of Blood Glucose Are Related to laboratory Measures of Insulin Sensitivity and Epinephrine Counterregulation", Diabetes Technology & Therapeutics, vol. 13, No. 1, 2011, pp. 11-17.
Zucchini, et al., "Comparison Between Sensor-Augmented Insulin Therapy with Continuous Subcutaneous Insulin Infusion or Multiple Daily Injections in Everyday Life: 3-Day Analysis of Glucose Patterns and Sensor Accuracy in Children", Diabetes Technology & Therapeutics, vol. 13, No. 12 (2011), pp. 1187-1193. XP55115470A.
Kovatchev, et al., "Assessment of Risk for Severe Hypoglycemia Among Adults With IDDM: Validation of the low blood glucose index", Diabetes Care, vol. 21, No. 11, Nov. 1998, pp. 1870-1875.

* cited by examiner

*Primary Examiner* — G Steven Vanni
(74) *Attorney, Agent, or Firm* — Dinsmore & Shohl, LLP (57) ABSTRACT

A system and technique are enclosed for determining the effectiveness of a blood glucose therapy treatment. Examples of this technique include analyzing sufficiency of blood glucose data collected from a patient with a computing device, analyzing hypoglycemic risk based on the blood glucose data with the computing device, analyzing glycemic control for the blood glucose data with the computing device, analyzing glycemic variability of the blood glucose data with the computing device, and outputting results from said analyzing the sufficiency, said analyzing the hypoglycemic risk, said analyzing the glycemic control, and said analyzing the glycemic variability with the computing device.

42 Claims, 8 Drawing Sheets

SYSTEM AND METHODS FOR ANALYZING BLOOD GLUCOSE DATA AND QUANTIFYING THE SUCCESS OR FAILURE OF INSULIN THERAPY

BACKGROUND

In the past few decades great technological strides have been made in the treatment and management of diabetes. With the advent of accurate home blood glucose monitors, diabetics are now able to perforin self-monitoring of blood glucose (SMBG) and perform multiple daily injections (MDI) of insulin therapies. The test most commonly involves pricking a finger or other body part with a lancet device to obtain a small blood sample, applying the sample to test strip, and determining glucose concentration via a glucose meter. If properly trained, diabetics can use the results to correct any deviations out of a desired target range by changing their carbohydrate intake, exercising, and/or adjusting the amount of insulin injected.

While multiple daily injection therapy is commonly recommended as an initial treatment option, continuous subcutaneous insulin infusion (CSII) therapy can be recommended for those "failing" multiple daily injection therapy. Failure is most often defined as an inability to reach glycemic goals without frequent hypoglycemia and/or increased glycemic variability. Health care insurance providers typically require a health care provider to find a failure in the multiple daily injection therapy before allowing reimbursement for the continuous subcutaneous insulin infusion therapy. There is, however, little guidance on how to quantify the success or failure of multiple daily injection therapy.

Traditionally, the management of diabetes has been based on Hemoglobin Al c (HbAlc), which includes a simple cut-off for good and bad. However, in addition to a serious increase in the risk of hypoglycemia observed in patients utilizing intensive therapies, recent studies have shown that HbAlc may not be enough. Evidence has shown an HbAlc independent relationship between glycemic variability and complications. Today, yet another new technology, the continuous glucose monitor (CGM), is changing the way we think about diabetes. Continuous glucose monitors provide exponentially more information, such as for example 288 glucose values in a 24-hour period, and a more complete picture of glycemic control. The data generated by continuous glucose monitors have the potential to dramatically improve glycemic control, but at the same time, the massive amounts of information can be overwhelming to patients and health care professionals.

SUMMARY

According to at least one exemplary embodiment of the present disclosure, a system and method of determining the effectiveness of a blood glucose treatment for an individual are provided.

In at least one embodiment of the method of the present disclosure, the method of determining effectiveness of a blood glucose treatment therapy comprises analyzing sufficiency of blood glucose data collected from a patient with a computing device, analyzing hypoglycemic risk based on the blood glucose data with the computing device, analyzing glycemic control for the blood glucose data with the computing device, analyzing glycemic variability of the blood glucose data with the computing device, and outputting results from said analyzing the sufficiency, said analyzing the hypoglycemic risk, said analyzing the glycemic control, and said analyzing the glycemic variability with the computing device.

In at least one embodiment of the method of the present disclosure, the outputting of the results includes providing a recommendation to change from a multiple daily injection (MDI) therapy to a continuous subcutaneous insulin infusion (CSII) therapy when the blood glucose data fails any one of said analyzing acts.

In at least one embodiment of the method of the present disclosure, the analyzing the sufficiency includes calculating a first average testing frequency for the blood glucose data over a first period with the computing device, and determining with the computing device whether the first average testing frequency is below a first testing frequency limit. Further, an embodiment of the method may also comprise the step of reporting an inadequate testing frequency with the computing device when the first average testing frequency is below the first testing frequency limit. Moreover, an embodiment of the method may also comprise the step of calculating a second average testing frequency for the blood glucose data over a second period with the computing device when the first average testing frequency is below the first testing frequency limit, and determining with the computing device whether the second average testing frequency is below a second testing frequency limit. Additionally, an embodiment of the method may further comprise the step of reporting an inadequate testing frequency with the computing device when the second average testing frequency is below the second testing frequency limit.

In at least one embodiment of the present disclosure, the second period may be shorter than the first period. Additionally, the second period in at least one embodiment may be about 15 days. The first period in at least one embodiment may be about 30 days.

In at least one embodiment, the first testing frequency limit and/or second testing frequency limit may be four glucose tests per day.

In at least one embodiment of the present disclosure, analyzing the hypoglycemic risk includes evaluating the low blood glucose index (LBGI). Additionally, in at least one embodiment, outputting the results includes reporting that the risk of hypoglycemia is elevated when the LBGI is moderate or high.

In at least one embodiment of the present disclosure, the step of evaluating LBGI includes transforming the blood glucose data to a symmetric scale; assigning one or more risk values based on said transforming, and determining the LBGI based on an average of the risk values.

In at least one embodiment of the present disclosure, the step of transforming the blood glucose data includes generating a transformed blood glucose level (Transformed BG) using the following formula:

$$\text{Transformed BG} = 1.509 \times \{[\log(BG)]^{1.084} - 5.381\}$$

where:
  BG=Blood Glucose Reading (mg/dL);
wherein said assigning the risk values are assigned as follows:
  If Transformed BG<0, then $$\text{Risk(BG)} = 10 \times (\text{Transformed BG})^2$$

otherwise $$\text{Risk(BG)} = 0$$

where:
  Risk (BG)=risk value for a blood glucose reading; and wherein said determining the LBGI is based on the following formula:

$$LBGI = \frac{\sum_{i=1}^{n} \text{Risk}(BG)_i}{n}$$

where:
n=number of blood glucose readings.

In at least one embodiment of the present disclosure, the hypoglycemic risk is: minimal when LBGI≤1.1; low when 1.1<LBGI≤2.5; moderate when 2.5<LBGI≤5.0; and high when LBGI>5.0.

In at least one embodiment of the present disclosure, the step of analyzing glycemic control includes evaluating a mean blood glucose level. Additionally, in at least one embodiment of the present disclosure, the step of outputting the results includes reporting that glycemic control is suboptimal when the mean blood glucose level exceeds a limit. The limit in at least one embodiment can be 154 mg/dL.

In at least one embodiment of the present disclosure, the step of analyzing glycemic variability includes calculating a standard deviation of the blood glucose data with the computing device, and evaluating the standard deviation with respect to a limit with the computing device. Further, the method in at least one embodiment further comprises determining with the computing device whether two times the standard deviation is greater than mean blood glucose level, and wherein said outputting the results includes reporting that glycemic variability is suboptimal in response to said determining that two times the standard deviation is greater than the mean blood glucose level. Additionally, in at least one embodiment of the present disclosure, the method further comprises the steps of determining with the computing device whether three times the standard deviation is greater than the mean blood glucose level, wherein said outputting the results includes reporting that glycemic variability is good in response to said determining that three times the standard deviation is greater than the mean blood glucose level.

In at least one embodiment of the present disclosure, the method further comprises determining with the computing device whether three times the standard deviation is less than or equal to the mean blood glucose level, wherein said outputting the results includes reporting that glycemic variability is excellent in response to said determining that three times the standard deviation is less than or equal to the mean blood glucose level.

In at least one embodiment of the present disclosure, outputting the results includes reporting therapy goals have been achieved when said analyzing the sufficiency, said analyzing the hypoglycemic risk, said analyzing the glycemic control, and said analyzing the glycemic variability with the computing device provide acceptable results.

In at least one embodiment of the present disclosure, the computing device includes a glucose meter. Additionally, in at least one embodiment the glucose meter may include a continuous glucose meter. Further, in at least one embodiment the method further comprises the step of collecting the blood glucose data with the glucose meter. Moreover, the method of the present disclosure in at least one embodiment further comprises providing to a third party payer a report recommending a change in the treatment therapy in response to said outputting results.

According to at least one embodiment of the system of the present disclosure, the system comprises a computing device having a non-transitory machine-readable storage medium comprising instructions that when performed by the computing device result in operations comprising: analyzing sufficiency of blood glucose data collected from a patient; analyzing hypoglycemic risk based on the blood glucose data; analyzing glycemic control for the blood glucose data; analyzing glycemic variability of the blood glucose data; and generating a report that provides the results from said analyzing the sufficiency, said analyzing the hypoglycemic risk, said analyzing the glycemic control, and said analyzing the glycemic variability.

In at least one embodiment of the present disclosure, the system further comprises a glucose meter. Further, at least one embodiment of the computing device of the present disclosure includes an input/output device.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. For instance, logical, mechanical, and electrical changes may be made without departing from the spirit and scope of the present disclosure.

Systems and techniques as described herein have been developed which, in at least one embodiment, can quantify the success or failure of a multiple daily injection therapy in a relatively simple and easy to understand manner. This technique may be especially helpful to demonstrate to third parties, such as health insurance companies, the need to change or adjust the therapy being used to treat a patient. For instance, the results from this analysis technique can be provided to a third-party to aid in obtaining reimbursement for continuous subcutaneous insulin infusion therapy.

Generally speaking, with this technique, the glycemic control, glycemic variability, and risk of hypoglycemia of the patient may be compared to other values to make a determination on the overall success or failure of the therapy. More particularly, at least one exemplary embodiment of the technique includes the stages of: determining data sufficiency, calculating risk of hypoglycemia, calculating glycemic control, and calculating glycemic variability.

For the data sufficiency stage, the average testing frequency may be used to determine whether there is sufficient information to determine the overall success or failure of the therapy for the patient. The average testing frequency may initially be calculated over the past 30 days. If the average testing frequency is less than four times per day, the average testing frequency may be calculated again over a defined past period of time, such as the past 15 days. If the average testing frequency is above a set amount for the defined period, such as four times per day for either the prior 15 or 30 days, then the analysis continues. Otherwise, the user is alerted that the data is insufficient.

During the hypoglycemia risk calculation stage, the Low Blood Glucose Index (LBGI) is used to determine the risk of hypoglycemia. If the Low Blood Glucose Index is high, then there is an increased risk of hypoglycemia, and the multiple daily injection or other therapy is more likely to be failing.

In the glycemic control calculation stage, the mean blood glucose is used to determine glycemic control by comparing the mean blood glucose level to a predetermined value. For example, if the mean blood glucose is greater than 154 mg/dL, the overall glycemic control is suboptimal and the therapy is likely to be failing.

When in the glycemic variability calculation stage, the standard deviation is used to determine the degree of glycemic variability by comparing the standard deviation to the mean blood glucose. For example, in an exemplary stage, if twice the standard deviation is greater than the mean blood glucose, the glycemic variability is suboptimal. If three times the standard deviation is less than or equal to the mean blood glucose, then glycemic variability is excellent. If the mean blood glucose is less than twice the standard deviation but more than three times the standard deviation, glycemic variability is good.

In at least one example, if the average daily testing frequency over the past 30 days is greater than or equal to four, the low blood glucose index is minimal or low, the mean blood glucose is less than 154 mg/dL, and two times the standard deviation is less than or equal to the mean blood glucose, then the therapy goals are determined to have been achieved. On the other hand, if the above criteria are not satisfied, the therapy, such as a multiple daily injection therapy, is determined to have not been successful and the patient may need to switch to another therapy, like a continuous subcutaneous insulin infusion therapy. The results of this analysis can aid in demonstrating to third parties, such as health insurance companies, that a patient needs to change or adjust therapies.

Figure 1:
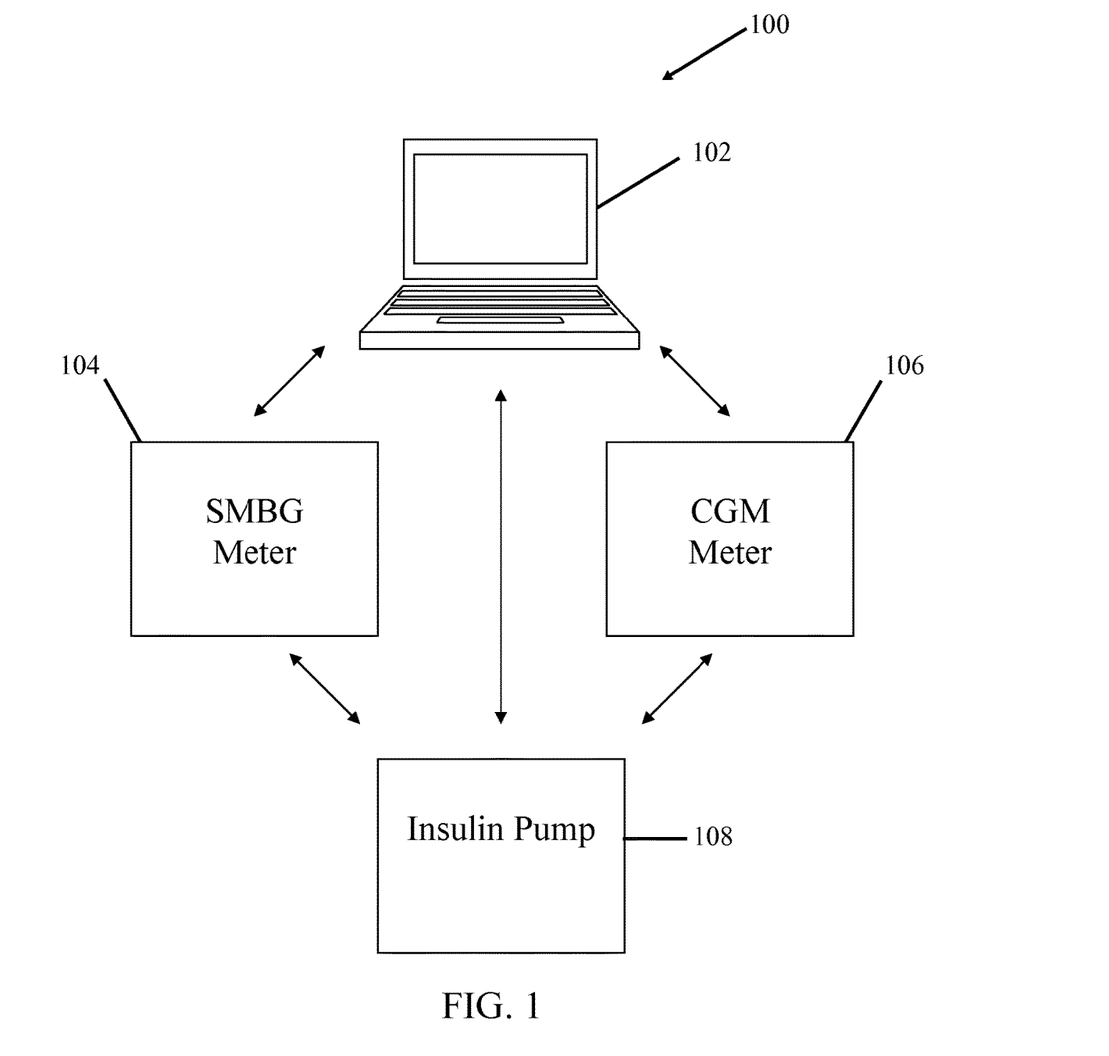
FIG. 1 is a diagram of a glucose monitoring system that determines the effectiveness of multiple daily injection therapy, according to at least one embodiment of the present disclosure.

FIG. 1 illustrates a glucose monitoring system 100 according to at least one embodiment of the present disclosure. Exemplary system 100 includes a computer 102, a self-monitoring blood glucose (SMBG) or discrete meter 104, a continuous glucose monitoring (CGM) device or meter 106, and/or an insulin pump 108. The computer 102 is operable to analyze data from the other components of the system 100, such as the meters 104, 106 and the insulin pump 108. Further, the self-monitoring blood glucose meter 104 in at least one embodiment is used to perform discrete blood glucose tests throughout the day for a multiple daily injection routine in which a diabetic injects insulin at various times via a syringe or an injection device. As will be explained in greater detail below, glucose readings from the self-monitoring blood glucose meter 104 can also be used to determine whether a change in therapy is required. This technique may in some instances be used to determine whether a multiple daily injection regiment is effective or if the user needs to switch over to using the insulin pump 108.

In the illustrated embodiment, the computer 102 includes at least one processor that executes software and/or firmware code stored in memory of computer 102. The software/firmware code contains instructions that, when executed by the processor of computer 102, causes computer 102 to perform the functions described herein. For example, computer 102 may have various types of software, including but not limited to CareLink® Pro, DexCom DM® 3, and Abbott Copilot® brand software to name just a few examples. Computer 102 may alternatively include one or more application-specific integrated circuits (ASICs), field-programmable gate arrays (FPGAs), digital signal processors (DSPs), hardwired logic, or combinations thereof. While computer 102 is illustratively a personal computer, other suitable devices may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although computer 102 is illustrated as a single computing device, multiple computing devices may be used together to perform the functions of computer 102 described herein.

As depicted by the arrows in FIG. 1, the computer 102 is configured to communicate with the self-monitoring blood glucose meter 104, the continuous glucose monitoring device or meter 106, and/or the insulin pump 108 in any number of manners, such as through a wired and/or wireless connection. Such wireless communications may be radio frequency ("RF") or other suitable wireless frequency, in which the measured glucose results are transmitted via electromagnetic waves. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. The communication may be unidirectional (i.e., data is transmitted only from glucose sensor 106 to computer 102) or bidirectional (i.e., data is transmitted between glucose sensor 106 and computer 102 in either direction). Furthermore, the communication may also facilitate communication between two or more devices, such as between glucose sensor 106, computing device 102, insulin pump 108, and other suitable devices or systems. In addition, a wired link may alternatively be provided, such as, for example, a wired Ethernet link. Other suitable public or proprietary wired or wireless links may also be used. The connection may be used to transmit data such as blood glucose measurements or results from a process performed on blood glucose measurement data. The connection may also be used to configure the parameters or settings on self-monitoring blood glucose meter 104, continuous glucose monitoring meter 106, and/or the insulin pump 108.

In at least one embodiment, computer 102 is in communication with a remote computing device, such as at a caregiver's facility or a location accessible by a caregiver, and data (e.g., glucose data or other physiological information) is transferred between them. In this embodiment, computer 102 and the remote device are configured to transfer physiological information through a data connection such as, for example, via the Internet, cellular communications, or the physical transfer of a memory device such as a diskette, USB key, compact disc, or other portable memory device.

In one particular example, the self-monitoring blood glucose meter 104 includes an ACCU-CHEK® Expert brand meter. The ACCU-CHEK® Expert brand meter is capable of storing glucose, meal, insulin, and other event information. All of this information can be easily uploaded to the computer 102 where the data can undergo further analysis and interpretation. It nevertheless should be appreciate that other kinds of meters can be used.

The insulin pump 108 can be connected to the self-monitoring blood glucose meter 104, the continuous glucose monitoring meter 106, and/or the computer 102. The connection may be used to transmit data from the self-monitoring blood glucose meter 104, the continuous glucose monitoring meter 106, and/or the computer 102 to the insulin pump 108 or vice versa. For example, the electronic connection may also be used to transmit instructions from the self-monitoring blood glucose meter 104 and/or the continuous glucose monitoring meter 106 to the insulin pump 108 regarding one or more injections of insulin from the pump into the patient. Additionally, the connection may transmit information regarding past, present, or future injections or insulin levels from the insulin pump 108 to the self-monitoring blood glucose meter 104 and/or the continuous glucose monitoring meter 106. Similar to the electronic connection discussed above, the connection between the self-monitoring blood glucose meter 104, the continuous glucose monitoring meter 106, and/or the insulin pump 108 may be wired or wireless and may be the same or a different type of connection than the one between the meter 104, meter 106, and/or the computer 102. It should be recognized that the system 100 in other embodiments can include different components, combinations of other components, and/or configured differently than is shown in FIG. 1.

Figure 2:
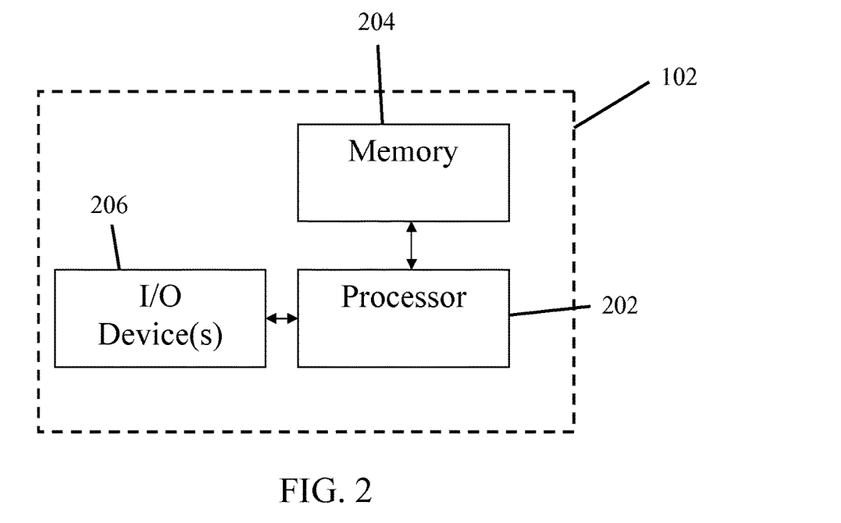
FIG. 2 is a block diagram of a computer shown in FIG. 1, according to at least one embodiment of the present disclosure.

FIG. 2 illustrates a block diagram of one example of the computer 102 illustrated in FIG. 1. As shown, the computer 102 includes a processor 202, memory 204, and/or an input/output (I/O) device(s) 206. The processor 202 is used to process information and commands, and the memory 204 stores data, such as glucose readings, structured tests, various functions, and procedures. For instance, the processor 202 can include a microprocessor and/or other electronics that are configured to process data, and the memory 204 is used to store data on a permanent or temporary basis.

The memory 204 is any suitable computer readable medium that is accessible by the processor 202. The memory 204 may be a single storage device or multiple storage devices, may be located internally or externally to computer 102, and may include both volatile and non-volatile media. Further, the memory 204 may include one or both of removable and non-removable media. Exemplary memory 204 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by computer 102.

The I/O device(s) 206 is used to enter data and provide information. The I/O device 206 can include a tactile input, buttons, touch screens, displays, speakers, and/or printers, but it can also include other types of I/O devices. It should be appreciated that the computer 102 can include other components and/or be configured differently in other embodiments.

I/O device 206 in an exemplary embodiment may display the estimated glucose state of the person and/or a predicted glucose state of the person at some time in the future. The glucose state may include the estimated glucose level and/or the estimated rate-of-change of the glucose level. The displayed information may also include an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 milligrams of glucose per deciliter of blood (mg/dl). Computer 102 may also be configured to tactilely communicate information or warnings to the person, such as for example by vibrating.

Figure 3:
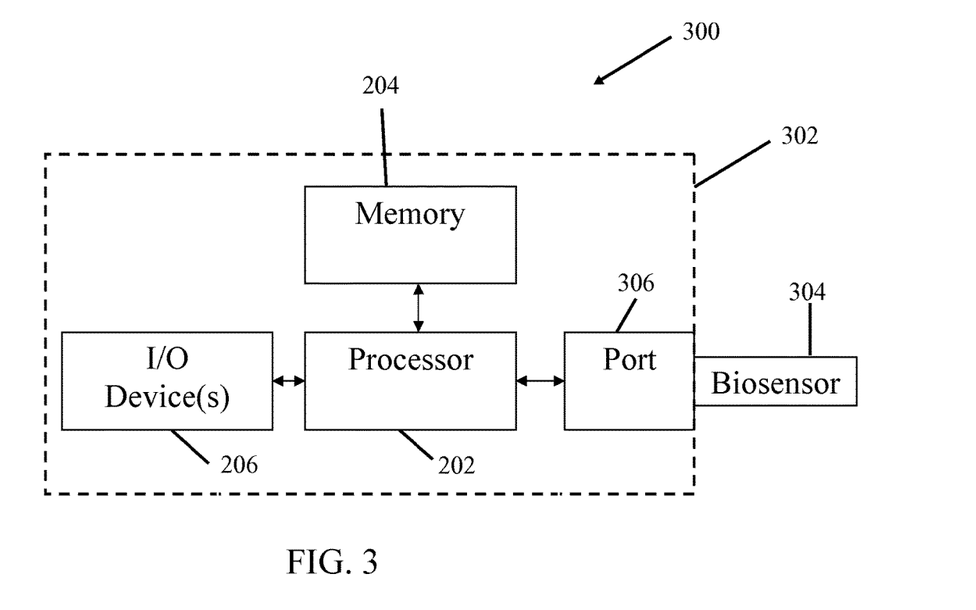
FIG. 3 is a block diagram of the meters shown in FIG. 1, according to at least one embodiment of the present disclosure.

It should be appreciated that the self-monitoring blood glucose meter 104 and the continuous glucose monitoring meter 106 can be configured in any number of manners. FIG. 3 illustrates just one example of a meter system 300 that includes a meter 302 and a biosensor 304 for analyzing a body fluid sample. The biosensor 304 can include a discrete test strip and/or continuous monitoring probe. The meter 302 shown in FIG. 3 generally represents the components found in the self-monitoring blood glucose meter 104 and the continuous glucose monitoring meter 106. As illustrated, the meter 302 includes the processor 202, memory 204, and an input/output (I/O) device(s) 206 of the type described above. The meter further includes a port 306 where the biosensor 304 is connected to the meter 302. The processor 202 is used to process information and commands, and the memory 204 stores information, such as blood glucose measurements, and other information. The meter 302 can include additional ports 306 to connect additional biosensors to measure a plurality of features such as body temperature, pulse, and/or blood oxygen content.

Figure 4:
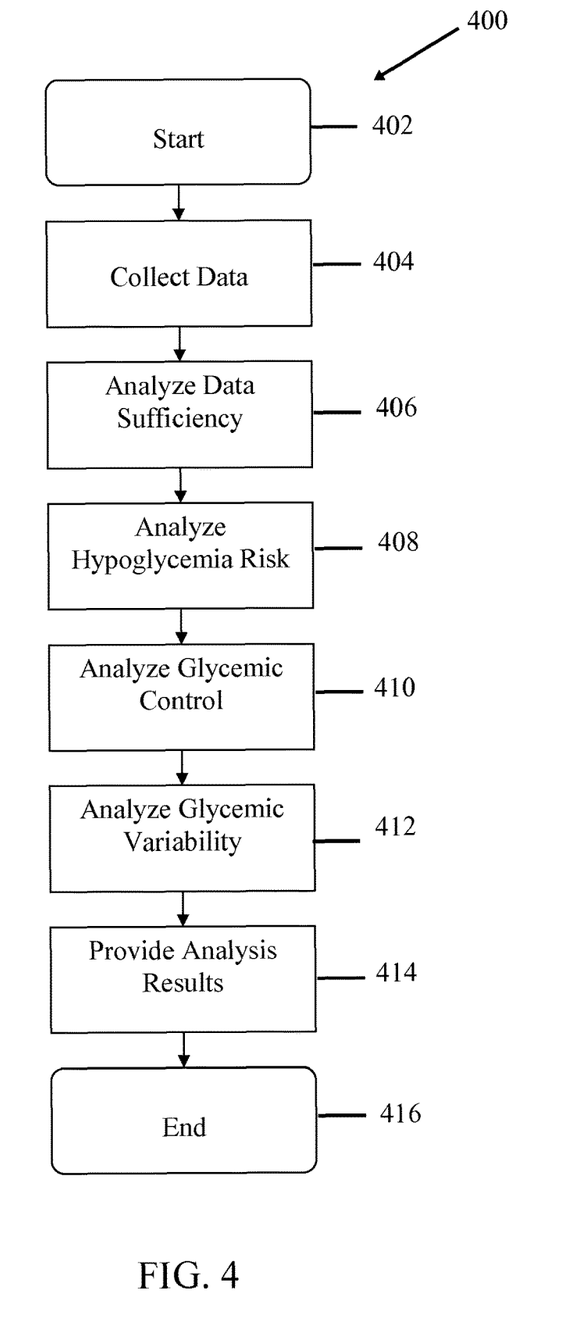
FIG. 4 is a flowchart illustrating a technique for analyzing data to determine the success of a therapy, according to at least one embodiment of the present disclosure.

As mentioned before, the data generated by continuous glucose monitors 106 have the potential to dramatically improve glycemic control, but at the same time, the massive amounts of information can be overwhelming to patients and health care professionals. In particular, interpretation of the results from continuous glucose monitors 106 can be quite difficult to understand. This in turn can make it hard for health care providers to back recommendations for changing or switching from different treatment therapies, such as from a multiple daily injection therapy to a continuous subcutaneous insulin infusion therapy using the insulin pump 108. FIG. 4 shows a flowchart 400 that illustrates an overview of a technique for quantifying the success or failure of a treatment therapy, such as a multiple daily injection therapy, in a relatively simple and easy to understand manner. This technique can be especially helpful to demonstrate to third parties, such as health insurance companies, the need to change or adjust the therapy being used to treat a patient. By way of a non-limiting example, the results from this analysis technique in FIG. 4 can be provided to a third-party to aid in obtaining reimbursement for continuous subcutaneous insulin infusion therapy using the insulin pump 108.

For explanation purposes, the technique in FIG. 4 will described as being performed by the computer 102, but it should be appreciated that this technique can be performed using other devices, such as the meters 104, 106, and/or insulin pump 108. It should be appreciated that the computer 102 (or other devices) performs the acts in this technique through the processor 202, memory 204, I/O device 206, and/or other components. For the sake of clarity as well as brevity, the computer 102 will be described as performing these acts, but it should be recognized that the acts are performed by the various components of the computer 102, such as the processor 202, memory 204, and the I/O device 206. Turning to FIG. 4, after starting the technique in stage 402, glucose and other data is collected in stage 404. Glucose readings in stage 404 can be collected in any number of manners, such as through the continuous glucose meter 106 either alone or in combination with the discrete meter 104. In other examples, one or more of the meters 104, 106 can be used for data collection and/or other devices can be used to aid data collection in stage 404. The computer 102 uploads or otherwise obtains the glucose and other data, and the collected data from stage 404 is analyzed by the computer in stage 406 to determine whether the amount and/or quality of the collected data is sufficient so as to provide useable results for proper analysis. In stage 408, the computer 102 analyzes the data to determine whether or not the risk of hypoglycemia has exceeded a specific threshold. The computer 102 in stage 410 analyzes the data so as to determine whether glycemic control has been achieved, and in stage 412, the computer determines whether the glycemic variability is within a specified threshold. The computer 102 via the I/O device 206 provides the results of the analysis in stage 414. For instance, the results of the analysis can be displayed on a screen and/or printed on a printer, or provided through auditory or tactile cues. Once the results are provided, the technique concludes in stage 416 or the computer 102 can start the analysis process again in stage 402. It should be understood that the various stages in FIG. 4 can occur in a different order than is shown, and selected stages can occur multiple times or even simultaneously. For example, if the computer 102 determines that the data is insufficient in stage 406, this result (stage 414) can be immediately provided without the need to perform the remaining acts.

A specific example of this technique will now be described with reference to a flowchart 500 shown in FIGS. 5, 6, 7, and 8. For explanation purposes, the technique illustrated by the flowchart 500 will be described with reference to the continuous glucose monitor 106 as collecting the glucose data and the computer 102 analyzing the collected data. However, it again should be recognized that other devices can be used to perform those acts in other examples. Moreover, for explanation purposes, this technique will be described as determining whether a multiple daily injection therapy has been successful or if a change in therapy is required. For example, this technique can be used to determine if a patient should switch to using the insulin pump 108. It should be appreciated that this technique can be used to determine the effectiveness of other diabetes treatment therapies.

Figure 5:
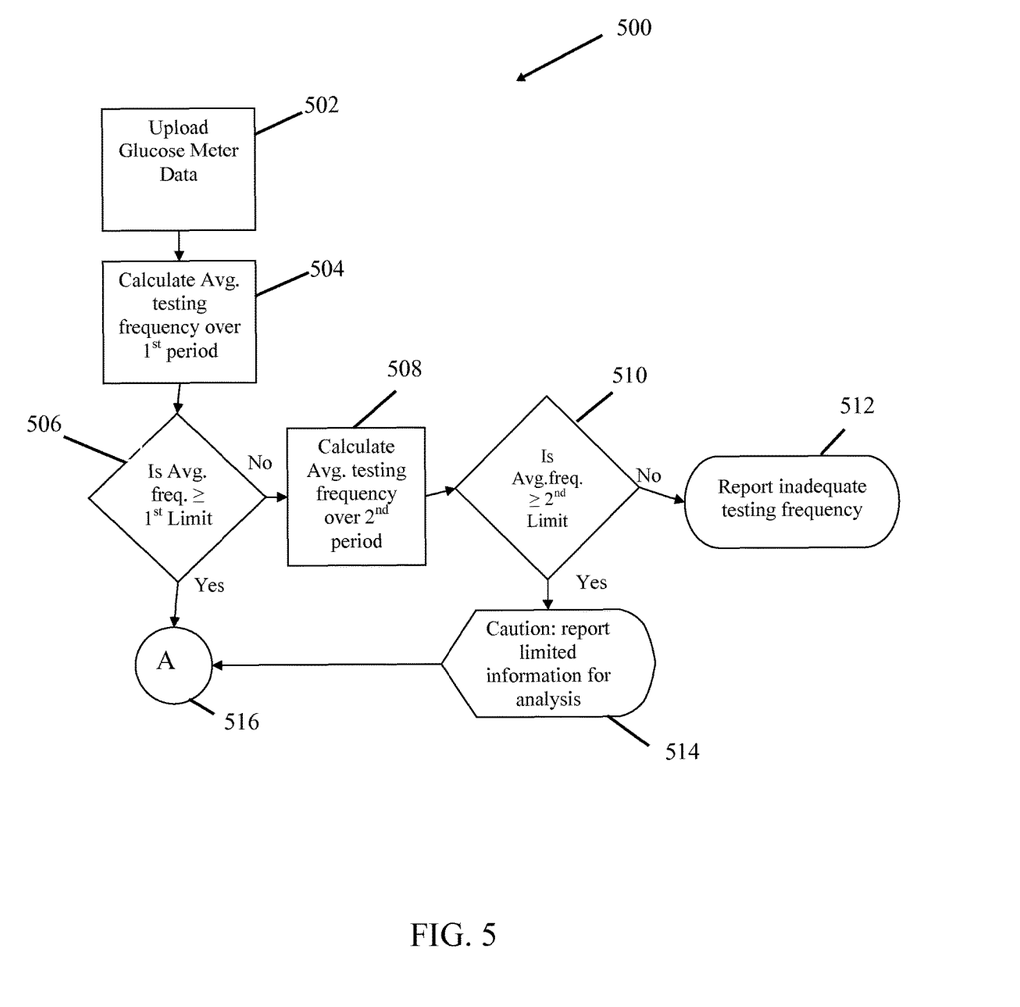
FIGS. 5, 6, 7, and 8 include a flowchart that illustrate a technique for determining the success of a glucose treatment therapy, according to at least one embodiment of the present disclosure.

Looking at FIG. 5, the continuous glucose meter 106 collects glucose measurements that in stage 502 are uploaded to the computer 102 (stage 404 in FIG. 4). As noted before, the continuous glucose meter 106 is able to provide a large data set for analysis, but this large amount of data can make it difficult in determining the effectiveness of a therapy using conventional analysis techniques. Again, the technique illustrated by the flowchart 500 provides a straightforward and effective way to analyze large amounts of glucose data to determine whether the therapy goals have been achieved. To analyze whether the glucose data is sufficient for analysis (stage 406 in FIG. 4), the computer 102 calculates the average testing frequency over a first specified period in stage 504. For example, the computer 102 can calculate average number of daily glucose tests over a 30 day period. However, this period can be different in other examples. In stage 506, the computer 102 determines if the average testing frequency is greater than or equal to a first limit. Returning to the previous example, the first limit can be 4 glucose tests per day, but the limit can be different in other situations. If the testing frequency is less than the limit specified in stage 506, the computer 102 then calculates the testing frequency over a second period in stage 508. In one embodiment, the length of the second period in stage 508 is shorter than the length of the period in stage 504. For instance, when the length of the first period is the last 30 days (stage 504), the length of the second period in stage 508 can be the last 15 days. In stage 510, the computer 102 determines whether the average testing frequency for the second period is greater than or equal to a second limit. The second limit in stage 510 can be the same as or different from the limit in stage 506. Returning to the previously mentioned example, the second limit in stage 510 is the same as the first limit, that is, 4 tests per day. If the average testing frequency is below the second limit (e.g., below 4 tests per day), the computer 102 via the I/O device 206 reports that the testing frequency is inadequate to perform proper analysis in stage 512. On the other hand, if in stage 510 the average testing frequency meets or exceeds the second limit (e.g., at or above 4 tests per day), the computer 102 provides a caution via the I/O device 206 that the analysis was based on limited information in stage 514. If the testing frequencies in stages 506 or 510 meet or exceed the specified limits, the computer 102 proceeds via connector 516 in FIGS. 5 and 6 to analyze the hypoglycemic risk (stage 408 in FIG. 4).

As can be appreciated, other methods of determining the sufficiency of the data may be used. For example, instead of determining the frequency of blood glucose measurements over a period of time, the computer 102 can simply calculate the number of blood glucose measurements and compare that to one or more predetermined values and/or calculated values. For example, the predetermined value may be thirty (30) and therefore the computer 102 may require that at least thirty (30) measurements are taken in determining the overall success or failure of the therapy.

Figure 6:
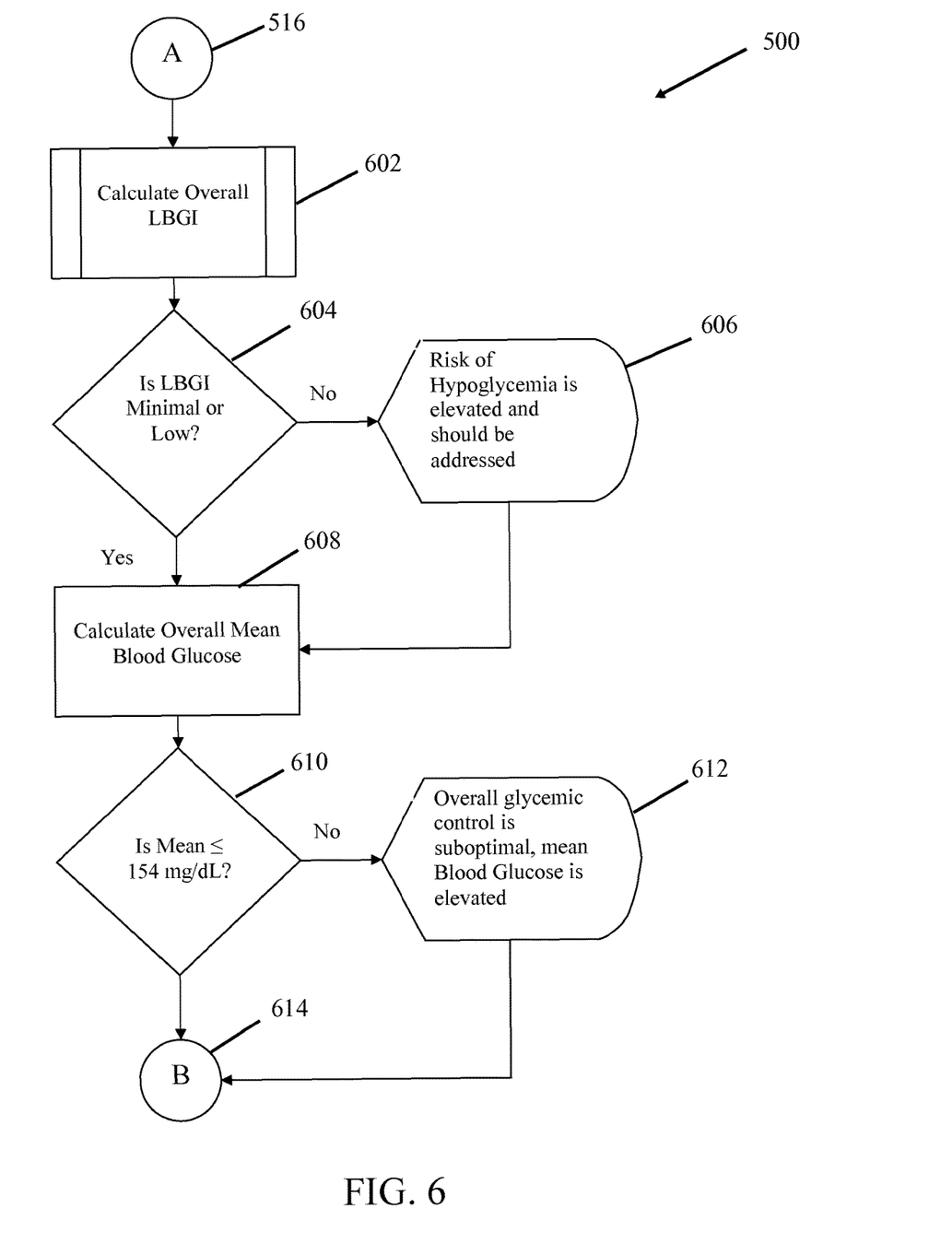

Turning to FIG. 6, the computer in stage 602 calculates the low blood glucose index (LBGI) based on the collected glucose data. Although hypoglycemia can be captured to some degree in the analysis of glycemic variability, given that a hypoglycemic condition presents an immediate concern in the management of diabetes, hypoglycemia is significant enough to prompt its own assessment. For instance, hypoglycemia can have deadly consequences in the very short term, leading to the patient fainting, having a seizure, going into a coma, and potentially leading to death. The unequal distribution of blood glucose values means that high glucose values can inflate the average, thereby diminishing the significance of hypoglycemia. In particular, the ranges for hypoglycemia as compared to hyperglycemia are dramatically different. In particular, the hyperglycemic range is numerically much greater that the hypoglycemic range such that the scale skewed. To address this issue, the low blood glucose index has been developed to provide a logarithmic type blood glucose data transformation that symmetrizes the blood glucose readings. Generally speaking, the higher the low blood glucose index, the greater the risk of severe hypoglycemia. The low blood glucose index can be calculated by the following equations. First, the blood glucose readings are transformed so as to make them symmetric around zero (0) with a range between −10.5 and +10.5. Equation 1 below shows how the blood glucose readings are transformed.

$$\text{Transformed BG} = 1.509 \times \{[\log(BG)]^{1.084} - 5.381\} \quad \text{Equation 1}$$

where:
BG=Blood Glucose Reading (mg/dL)

It should be recognized that Equation 1 can differ depending on the measurement units for the blood glucose readings (e.g, mmol/L instead of mg/dL). Risk values are then assigned to each transformed blood glucose values as follows in Equation 2:

If Transformed BG<0, then $$\text{Risk(BG)} = 10 \times (\text{Transformed BG})^2$$

otherwise $$\text{Risk(BG)} = 0 \quad \text{Equation 2}$$

where:
Risk (BG)=risk value for a blood glucose reading.

The low blood glucose index (LBGI) is the average of the risk values for all of the blood glucose readings, and the low blood glucose index can be represented by Equation 3.

$$LBGI = \frac{\sum_{i=1}^{n} \text{Risk}(BG)_i}{n} \quad \text{Equation 3}$$

where:
n=number of blood glucose readings.

The low blood glucose index is a summary statistic that increases when the frequency and/or extent of low blood glucose readings occur. A higher low blood glucose index value can indicate a record of numerous mild low blood glucose readings, a few extreme low blood glucose readings, or some combination of thereof. More information about the low blood glucose index (LBGI) can be found at Kovatchev B P, Cox D J, Gonder-Frederick L A, Clarke W L: "Symmetrization of the Blood Glucose Measurement Scale and its Applications" Diabetes Care 20:1655-1658, 1997, and Kovatchev, BP et al.: "Assessment of Risk for Severe Hypoglycemia Among Adults with IDDM: validation of the low blood glucose index" Diabetes Care 21:1870-1875, 1998, which are hereby incorporated by reference.

Again, the most immediate concern in the management of diabetes is hypoglycemia because hypoglycemia can have deadly consequences in the short term. An initial low blood glucose index calculation and assessment can draw attention to the most immediate concern. In stage 602, the low blood glucose index can be calculated for the entire period and/or on a day-by-day basis to draw attention to individual days that have a high frequency of hypoglycemia. The computer 102 in stage 604 compares the low blood glucose index to one or more predetermined thresholds to determine whether the low blood glucose index is acceptable. In particular, the computer 102 determines if the low blood glucose index is minimal or low. Table 1 below provides an example of ranges for categorizing the low blood glucose index levels.

TABLE 1

| Low Blood Glucose Index (LBGI) Range | Risk Level |
| --- | --- |
| LBGI ≤ 1.1 | Minimal Risk |
| 1.1 < LBGI ≤ 2.5 | Low Risk |

TABLE 1-continued

| Low Blood Glucose Index (LBGI) Range | Risk Level |
| --- | --- |
| 2.5 < LBGI ≤ 5.0 | Moderate Risk |
| LBGI > 5.0 | High Risk |

It should be appreciated that other ranges can be used to establish threshold levels different than those shown in Table 1. When the risk level is moderate or high (e.g., LBGI>2.5 in Table 1), the computer 102 proceeds to stage 606 where it is indicated that the risk of hypoglycemia is elevated and should be addressed. For instance, the I/O device 206 of the computer 102 can display and/or print out a report warning that the risk of hypoglycemia is elevated. Alternatively or additionally, such a warning can be provided later so as to aggregate all of the issues into a single report.

As noted before with respect to FIG. 4, the technique also determines glycemic control (stage 410). For the particular technique illustrated with the flowchart 500 in FIG. 6, the determination of glycemic control is based on the mean blood glucose level over the relevant period. Among all of the measures designed to capture the overall picture of glycemic control, none has really improved upon the average or mean of all glucose values. Despite the fact that the range of glucose values are skewed and an average is to some degree inflated by the extremely high values, the mean or average blood glucose level is highly correlated with HbA1c and is easy to both calculate and understand. The computer in stage 608 calculates the overall mean blood glucose level for the relevant period (e.g., for the last 30 days). In stage 608, the mean blood glucose level can be calculated for the overall period and/or on each day. Calculating the mean on a daily basis helps to assess whether the desired level of control has been achieved on a given day. The computer 102 in stage 610 determines whether the one or more calculated mean blood glucose levels exceeded a specified limit. This test can be represented by Equation 4 below.

$$\mu \leq \text{Upper Limit} \quad \text{Equation 4}$$

where:
μ=Mean Blood Glucose Level
Upper Limit=Blood Glucose Level Upper Limit

In the illustrated example, this upper limit is 154 mg/dL, but it should be recognized that other limit values can be used. When the mean blood glucose target is above this limit (e.g., greater than 154 mg/dL), the computer in stage 612 notes that glycemic control is below optimal. Like before, the computer 102 in stage 612 can simply record in memory 204 this issue for later reporting purposes and/or provide a warning via the I/O device 206 that the mean blood glucose level is elevated and suboptimal. After stages 610 and 614, the technique proceeds to stage 702 in FIG. 7, as is depicted by connector 614.

As mentioned above with respect to stage 412 in FIG. 4, this technique also analyzes the glycemic variability of the collected data. Instead of using more complex measures of variability, this technique uses standard deviation as a measure of variability, because among other things, it allows for relatively easy calculations and is a concept most everyone is generally familiar with. The importance of glycemic variability can be demonstrated by using mean amplitude of glycemic excursion (MAGE). However, there is more than one way to calculate MAGE and considering the close relationship of MAGE to the standard deviation, using MAGE for determining glycemic variability may not be the best choice. The standard deviation for the blood glucose readings is much easier to calculate and may offer just as much information as MAGE.

Figure 7:
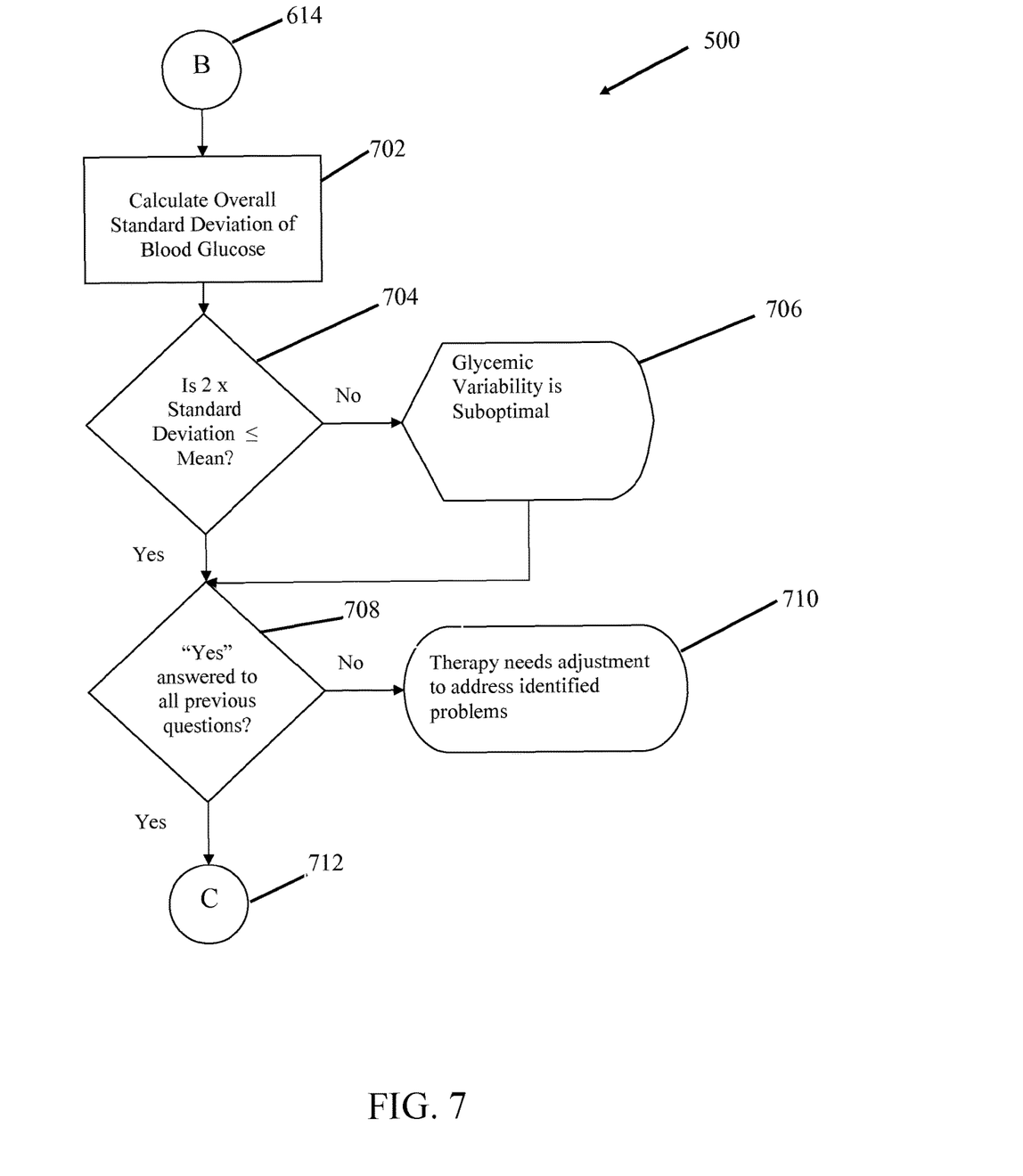

Turning to FIG. 7, the computer 102 in stage 702 calculates the overall standard deviation of the blood glucose readings. In stage 704, the computer 102 evaluates the calculated or target standard deviation to determine whether the variability of the blood glucose measurements is in control. As can be seen in the flowchart 500 of FIG. 7, the computer 102 in stage 704 determines whether double (2×) the calculated standard deviation is no more than the mean. To put it another way, the target standard deviation in stage 704 should be less than or equal to half of the mean blood glucose level calculated in stage 608. Equations 5 and 6 below represent this test in stage 704 in two different manners.

$$2 \times \sigma \leq \mu \qquad \text{Equation 5}$$

$$\sigma \leq \frac{\mu}{2} \qquad \text{Equation 6}$$

where:
  μ=Mean Blood Glucose Level
  σ=Glucose Level Standard Deviation

If the standard deviation fails the test in stage 704, the computer 102 indicates that the glycemic variability is below optimal in stage 706. For example, the computer 102 in stage 612 can simply record in memory 204 this issue for later reporting purposes and/or provide a warning via the I/O device 206 that the variability is suboptimal.

Based on the analysis, the computer 102 provides the results of the analysis (stage 414 in FIG. 4). Looking at stage 708 in FIG. 7, if the glucose data failed any of the previous tests (e.g., in stages 506, 510, 604, 610, or 704), then the computer 102 via the I/O device 206 provides a report in stage 710 indicating that the therapy needs to be adjusted so as to adjust a particular problem identified during the analysis. For example, if the data was found to be insufficient in stages 506 and 510, the computer 102 can indicate that the data was insufficient and recommend that the tests be performed using a continuous glucose meter 106, rather than via the discrete meter 104. As another example, if the hypoglycemia risk is found to be moderate or high in stages 604 and 606, the computer 102 can indicate that this is a problem and recommend a change in therapy. In still yet another example, when the computer 102 finds the glycemic variability to be suboptimal in stages 704 and 706, the computer 102 can alert the health care provider about the issue and suggest that the patient switch from a multiple daily injection routine to using the insulin pump 108. It should be appreciated that the glucose data may fail multiple tests in the analysis such that the computer 102 may report multiple problems at the same time.

Figure 8:
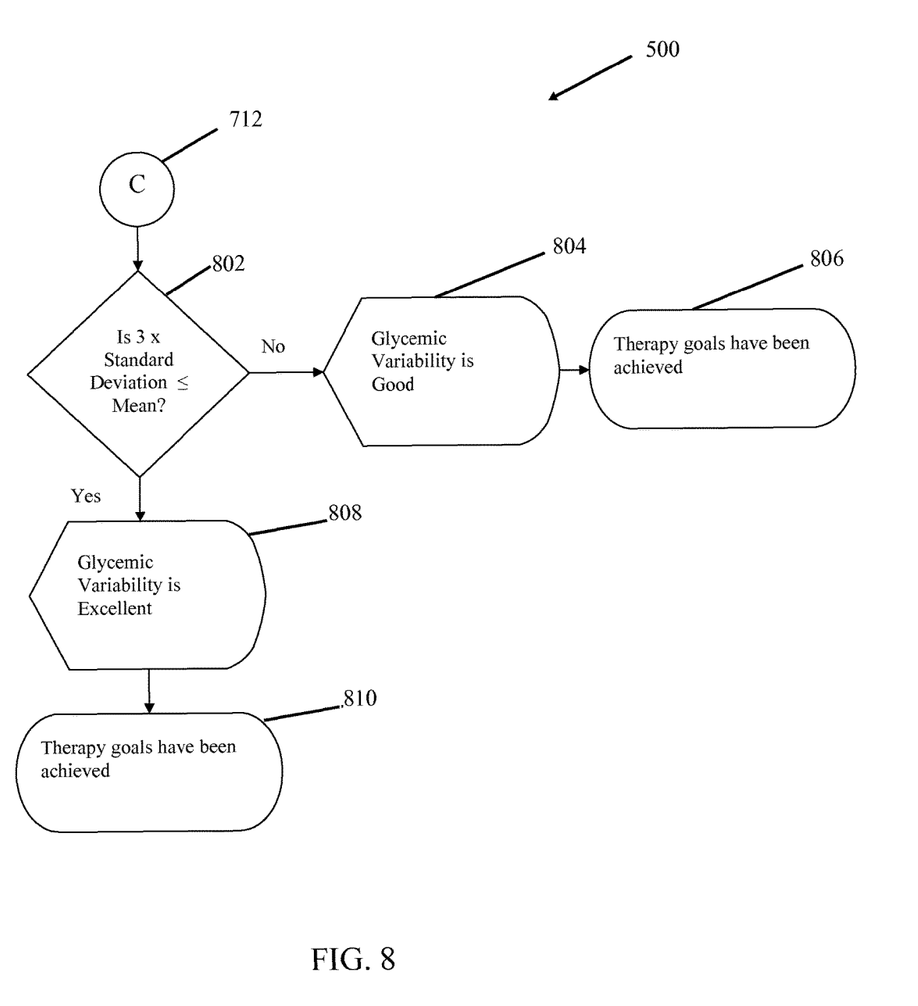

As indicated by connector 712 in FIGS. 7 and 8, after determining that the data has passed the previous tests in stage 708, the computer 102 then determines whether the glycemic control is good or excellent. Looking at stage 802 in FIG. 8, the computer 102 evaluates the standard deviation to determine whether the variability of the blood glucose measurements is in better control. As can be seen in the flowchart 500 of FIG. 8, the computer 102 in stage 802 determines whether three-times (3×) the calculated standard deviation is no more than the mean. To put it another way, the target standard deviation in stage 802 should be less than or equal to a third of the mean blood glucose level calculated in stage 608. Equations 7 and 8 below represent this test in stage 802 in two different manners.

$$3 \times \sigma \leq \mu \qquad \text{Equation 7}$$

$$\sigma \leq \frac{\mu}{3} \qquad \text{Equation 8}$$

where:
  μ=Mean Blood Glucose Level
  σ=Glucose Level Standard Deviation

If the standard deviation fails the test in stage 804, the computer 102 indicates that the glycemic variability is good in stage 804 and reports that the therapy goals have been achieved in stage 806. Otherwise, when the computer 102 in stage 802 determines that three-times (3×) the calculated standard deviation is no more than the mean glucose level, the computer 102 indicates that the glycemic variability is excellent in stage 808 and reports that the therapy goals have been achieved in stage 810. The computer 102 in stages 806 and 810 can for example simply provide such reports via the I/O device 206.

It should be recognized that the various stages shown in the flowchart 500 of FIGS. 5, 6, 7, and 8 can be performed in a different sequence shown. Moreover, various stages can be combined together so as to be performed simultaneously or near simultaneously. Further, other acts can be performed as well.

Figure 9:
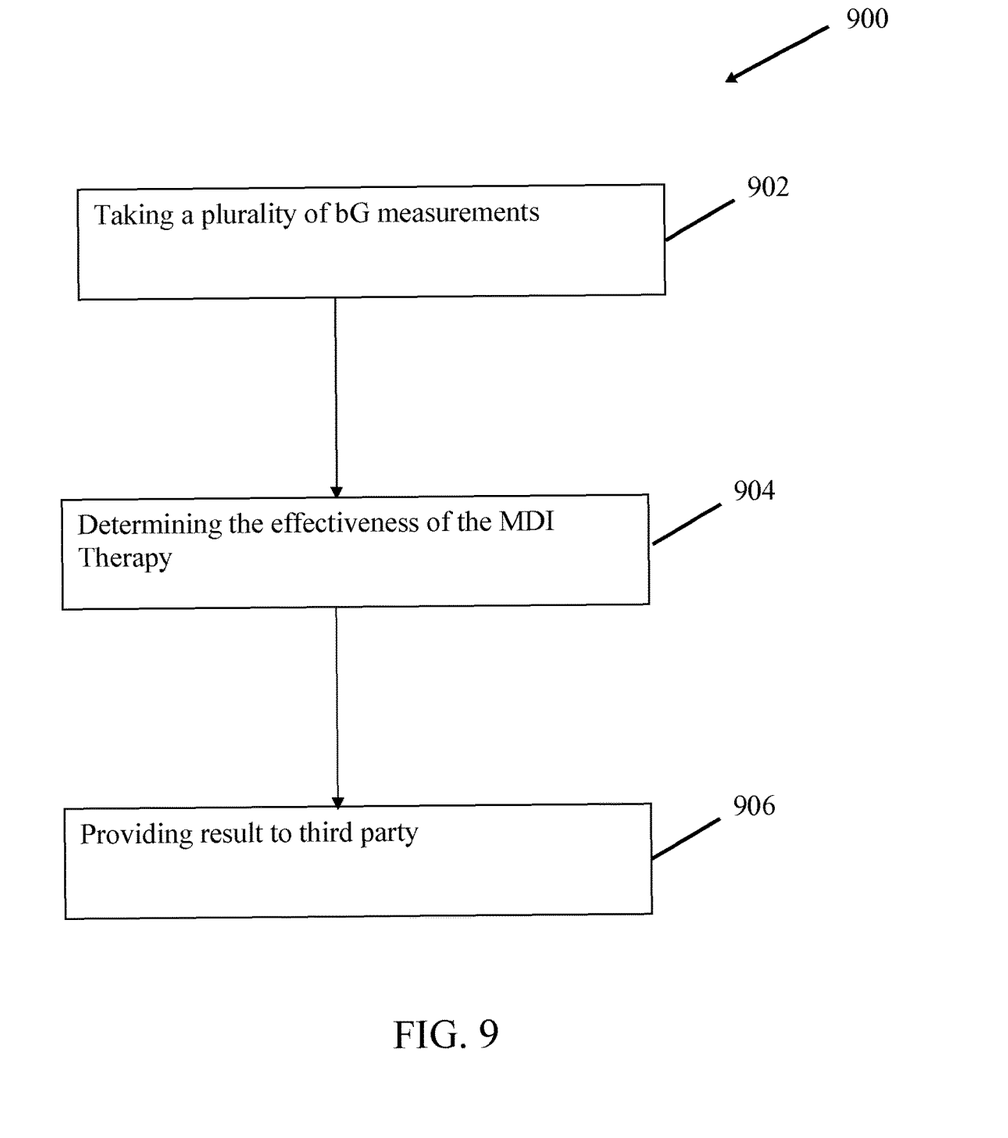
FIG. 9 is a flowchart illustrating a technique for providing results from the analysis to a third party, according to at least one embodiment of the present disclosure.

FIG. 9 illustrates a flow diagram 900 of one example of a method by which a third party is provided with the results of this analysis. In the illustrated example, the analysis is regarding the success or failure of a multiple daily injection therapy, but it should be understood that this method can be used for other types of therapies. Again, these results can be especially helpful to show third parties, such as health insurance companies, that a patient needs to change or adjust therapies. For example, a patient failing multiple daily injection therapy may need to change to a therapy using an artificial pancreas or an insulin pump. The results may also be used to prove the need to change a patient from a self-monitoring blood glucose meter to a continuous glucose monitoring meter. These results may not only be helpful in proving the need to change therapies but also in providing evidence to support reimbursement from a third party, such as a health insurance company, for the new therapy. Examples of third parties may include a health care provider, health insurance provider, health care network, physician, and/or person/entity selected by the patient or patient's physician.

In this example illustrated in FIG. 9, the discrete meter 104 takes a plurality of blood glucose measurements 902, determines the effectiveness of the multiple daily injection therapy 904 from that plurality of blood glucose measurements, and then provides a result of successful or unsuccessful therapy to a third party 906. The results may be provided to the third party directly from the meter 104 or it may be provided indirectly. For example, the result of a successful or failed therapy may be downloaded or read from the meter 104 using the I/O device(s) 206 during a patient's visit to a physician's office. Similarly, the meter 104 may be connected to a separate device, such as computer 102, and transmit the result from the meter 104 to the separate device. The separate device then may provide the result to the third party or to another separate device that routes the result to the third party.

The above described techniques provide a quantitative way to determine whether or not a person is failing a multiple daily injection therapy and whether a change to a continuous subcutaneous insulin infusion therapy is appropriate or even necessary. This allows a physician to provide concrete quantitative data to insurance companies or other health care payers to aid in obtaining reimbursement for insulin pumps. It should be understood that these techniques can be modified and/or used in conjunction with other other forms of assessment. These techniques can be more broadly utilized by physicians to obtain immediate information regarding glycemic control regardless of the therapy type used by the patient.

In one variation, an assessment of basal insulin can be performed by combining the mean fasting value with the low blood glucose index (LBGI). A high mean fasting blood glucose value with an elevated low blood glucose index would indicate the need for continuous subcutaneous insulin infusion in order to avoid the dawn phenomenon. For instance, the overnight period may be the only time where basal insulin can be truly assessed without any effects of rapid acting insulin. However, if there is a 4-hour or more gap between meals, the glucose level may be able to be used to assess the basal dose. This requires that the meal dose is sufficient to bring the glucose level back to the normal level. In either of these cases, a basal assessment would mean assessing the rate of change. If for example the rate of change in a 3- to 4-hour period is greater than 20 to 30 mg/dL in the negative direction, the recommendation would be to decrease the basal dose. On the other hand, if the change is in the positive direction, an increase in the basal dose is recommended.

In a further variation, these techniques can be used to aid in detecting contributing factors. Once the initial assessment of hypoglycemia, variability, and overall control is performed, additional information regarding the timing of the contributors can be considered. If the low blood glucose index is too high, indicating a risk of hypoglycemia, attention should be brought to the timing of the risk. When variability is an issue, the timing of the greatest change should be evaluated. If the overall mean blood glucose level is high, perhaps the longest period of time with elevated levels should be evaluated.

While various embodiments of systems and methods for determining the effectiveness of a blood glucose treatment therapy have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A computerized method of determining and reporting effectiveness of a blood glucose treatment therapy of multiple daily injections administered to a patient with diabetes which quantifies effectiveness as a success or failure of the administered blood glucose treatment therapy to reach glycemic goals based on blood glucose data collected from the patient via a biosensor, comprising:
    transmitting to a computing device via a wired and/or wireless connection blood glucose data collected from the patient via the biosensor;
    averaging blood glucose level readings from the biosensor in the blood glucose data per day over a first period and thereby determining a first average testing frequency;
    calculating a low blood glucose index (LBGI) with the computing device by:
        using a logarithmic formula which transforms each collected blood glucose level from the blood glucose data to a symmetric scale which addresses scale skewing that diminishes significance of hypoglycemia indicated in the blood glucose data;
        assigning a risk value to each transformed blood glucose level using a rule; and
        averaging the assigned risk values and thereby determining the LBGI;
    calculating a mean blood glucose level from the blood glucose data with the computing device;
    calculating a standard deviation of the blood glucose data with the computing device;
    determining with the computing device a failure of effectiveness of an administered blood glucose treatment therapy of the multiple daily injections administered to the patient with diabetes based upon:
        determining with the computing device that the first average testing frequency exceeds a first testing frequency limit which governs sufficiency of the blood glucose data collected from the patient for use in quantifying the failure or success of the effectiveness of the administered blood glucose treatment therapy, and
        determining with the computing device that one or more of the following conditions have been met:
            (i) the calculated LB GI exceeds a value for hypoglycemic risk,
            (ii) the calculated mean blood glucose level exceeds a limit for glycemic control, and
            (iii) the calculated standard deviation exceeds a limit for glycemic variability; and
    reporting by the computing device via an input/output (I/O) device a recommendation to change from a blood glucose treatment therapy of the multiple daily injections to a continuous subcutaneous insulin infusion (CSII) therapy upon the failure of the effectiveness of the administered blood glucose treatment therapy from determining by the computing device that the first average testing frequency exceeds the first testing frequency limit and the one or more of the conditions (i)-(iii) were met.

2. The method according to claim 1, further comprising reporting an inadequate testing frequency with the computing device when the first average testing frequency is below the first testing frequency limit.

3. The method according to claim 1, further comprising:
calculating a second average testing frequency for the blood glucose data over a second period with the computing device when the first average testing frequency is below the first testing frequency limit and
determining with the computing device whether the second average testing frequency is below a second testing frequency limit.

4. The method according to claim 3, further comprising reporting an inadequate testing frequency with the computing device when the second average testing frequency is below the second testing frequency limit.

5. The method according to claim 3, wherein the second period is shorter than the first period.

6. The method according to claim 3, wherein the second period is about 15 days.

7. The method according to claim 3, wherein the second testing frequency limit is 4 glucose tests per day.

8. The method according to claim 1, wherein the first period is 30 days.

9. The method according to claim 1, wherein the first testing frequency limit is 4 glucose tests per day.

10. The method according to claim 1, wherein said logarithmic formula used to generate the transformed blood glucose level (Transformed BG) is as follows:

Transformed BG=1.509×{[log (BG)]$^{1.084}$−5.381} where:
BG=Blood Glucose Reading (mg/dL); and
wherein said rule assigning the risk values is as follows:
If Transformed BG<0, then Risk (BG)=10×(Transformed BG)$^2$ otherwise Risk (BG)=0 where:
Risk (BG)=risk value for a blood glucose reading; and
wherein said determining the LBGI is based on the following formula:

$$LBGI = \frac{\sum_{i=1}^{n} \text{Risk}(BG)_i}{n}$$

where:
n=number of blood glucose readings.

11. The method according to claim 10, wherein the hypoglycemic risk is:
minimal when LBGI≤1.1;
low when 1.1<LBGI≤2.5;
moderate when 2.5<LBGI≤5.0; and
high when LBGI>5.0.

12. The method according to claim 11, wherein said reporting includes providing a warning that the risk of hypoglycemia is elevated when the LBGI is moderate or high.

13. The method according to claim 1, wherein said reporting includes providing a warning that glycemic control is suboptimal when the mean blood glucose level exceeds the limit for glycemic control.

14. The method according to claim 13, wherein the limit for glycemic control is 154 mg/dL.

15. The method according to claim 1, wherein the limit for glycemic variability is the mean blood glucose level and said method further comprises:
determining with the computing device whether two times the standard deviation is greater than the mean blood glucose level and
wherein said reporting includes providing a warning that glycemic variability is suboptimal in response to said determining that two times the standard deviation is greater than the mean blood glucose level.

16. The method according to claim 1, further comprising:
determining with the computing device whether three times the standard deviation is greater than the mean blood glucose level and
reporting by the computing device that glycemic variability is good in response to said determining that three times the standard deviation is greater than the mean blood glucose level.

17. The method according to claim 1, further comprising:
determining with the computing device whether three times the standard deviation is less than or equal to the mean blood glucose level and
reporting by the computer device that glycemic variability is excellent in response to said determining that three times the standard deviation is less than or equal to the mean blood glucose level.

18. The method according to claim 1, further comprising:
reporting by the computing device that therapy goals have been achieved upon none of the conditions (i)-(iii) being met.

19. The method according to claim 1, wherein the computing device includes a glucose meter.

20. The method according to claim 19, further comprising:
collecting the blood glucose data with the glucose meter.

21. The method according to claim 20, wherein the glucose meter includes a continuous glucose monitoring meter or a self-monitoring blood glucose meter.

22. The method according to claim 1, further comprising:
providing to a third party payer a report recommending a change in the treatment therapy in response to said reporting that the recommendation to change from the blood glucose treatment therapy of the multiple daily injections to a continuous subcutaneous insulin infusion (CSII) therapy.

23. The method according to claim 1, wherein the biosensor includes a discrete test strip and/or continuous monitoring probe.

24. The method according to claim 1, wherein the transmitting to the computing device via the wired and/or wireless connection of the blood glucose data collected from the patient via the biosensor is from a self-monitoring blood glucose meter, a continuous glucose monitoring meter, and/or the insulin pump.

25. The method of claim 1, wherein the I/O device is one or more of a touch screen, a display, a speaker, and a printer.

26. A system for determining and reporting effectiveness of a blood glucose treatment therapy of the multiple daily injections administered to a patient with diabetes which quantifies effectiveness as a success or failure of the administered blood glucose treatment therapy to reach glycemic goals based on blood glucose data collected from the patient via a biosensor, comprising:
a computing device comprising a non-transitory machine-readable storage medium comprising instructions that when executed by a processor of the computing device cause the computing device to:
receive, via a wired and/or wireless connection, blood glucose data collected from the patient via a biosensor;
average blood glucose level readings from the biosensor in the blood glucose data per day over a first period and which determines a first average testing frequency;
calculate a low blood glucose index (LBGI) by:
using a logarithmic formula which transforms each collected blood glucose level from the blood glucose data to a symmetric scale and which thereby addresses scale skewing that diminishes significance of hypoglycemia indicated in the blood glucose data;
assigning a risk value to each transformed blood glucose level via a rule; and
averaging the assigned risk values which determines the LBGI;
calculate a mean blood glucose level from the blood glucose data;
calculate a standard deviation of the blood glucose data;
determine a failure of effectiveness of an administered blood glucose treatment therapy of the multiple daily injections administered to the patient with diabetes based upon:
a determination that the first average testing frequency exceeds a first testing frequency limit which governs sufficiency of the blood glucose data collected from the patient for use in quantifying the failure or success of the effectiveness of the administered blood glucose treatment therapy and
a determination that one or more of the following conditions have been met:
(i) the calculated LBGI exceeds a value for hypoglycemic risk,
(ii) the calculated mean blood glucose level exceeds a limit for glycemic control, and
(iii) the calculated standard deviation exceeds a limit for glycemic variability; and
report via an input/output (I/O) device a recommendation to change from the blood glucose treatment therapy of the multiple daily injections to a continuous subcutaneous insulin infusion (CSII) therapy upon the failure of the effectiveness of the administered blood glucose treatment therapy from the determination that the first average testing frequency exceeds the first testing frequency limit and the one or more of the conditions (i)-(iii) were met.

27. The system according to claim 26, further comprising a glucose meter.

28. The system according to claim 26, wherein the biosensor includes a discrete test strip and/or continuous monitoring probe.

29. The system according to claim 26, wherein the computing device is communicatively coupled via the wired and/or wireless connection to a self-monitoring blood glucose meter, a continuous glucose monitoring meter, and/or the insulin pump which provide the blood glucose data collected from the patient via the biosensor.

30. The system according to claim 26, wherein said instructions further cause the computing device to report via the I/O device an inadequate testing frequency upon the first average testing frequency being below the first testing frequency limit.

31. The system according to claim 26, wherein said instructions further cause the computing device to:
calculate a second average testing frequency for the blood glucose data over a second period when the first average testing frequency is below the first testing frequency limit; and
determine whether the second average testing frequency is below a second testing frequency limit.

32. The system according to claim 31, wherein said instructions further cause the computing device to report via the I/O device an inadequate testing frequency with the computing device when the second average testing frequency is below the second testing frequency limit.

33. The system according to claim 31, wherein the second period is shorter than the first period.

34. The system according to claim 26, wherein said logarithmic based formula used to generate the transformed blood glucose level (Transformed BG) is as follows:

Transformed BG=1.509×{[log (BG)]$^{1.084}$−5.381} where:
BG=Blood Glucose Reading (mg/dL), and
wherein said rule to assign the risk values is as follows:
If Transformed BG<0, then Risk (BG)=10×(Transformed BG)$^2$ otherwise Risk (BG)=0 where:
Risk (BG)=risk value for a blood glucose reading, and
wherein the LBGI is determined based on the following formula:

$$LBGI = \frac{\sum_{i=1}^{n} \text{Risk}(BG)_i}{n}$$

where:
n=number of blood glucose readings.

35. The system according to claim 34, wherein the hypoglycemic risk is:
minimal when LBGI≤1.1,
low when 1.1<LBGI≤2.5,
moderate when 2.5<LBGI≤5.0, and
high when LBGI>5.0.

36. The system according to claim 35, wherein said instructions further cause the computing device to provide via the I/O device:
a warning that the risk of hypoglycemia is elevated when the LBGI is moderate or high, and
a warning that glycemic control is suboptimal when the mean blood glucose level exceeds the limit for glycemic control.

37. The system according to claim 26, wherein the limit for glycemic variability is the mean blood glucose level, and said instructions further cause the computing device to:
determine whether two times the standard deviation is greater than the mean blood glucose level, and
provide via the I/O device a warning that glycemic variability is suboptimal in response to a determination that two times the standard deviation is greater than the mean blood glucose level.

38. The system according to claim 26, wherein said instructions further cause the computing device to:

determine whether three times the standard deviation is greater than the mean blood glucose level and provide via the I/O device a report that glycemic variability is good in response to a determination that three times the standard deviation is greater than the mean blood glucose level.

39. The system according to claim 26, wherein said instructions further cause the computing device to:

determine whether three times the standard deviation is less than or equal to the mean blood glucose level and provide via the I/O device a report that glycemic variability is excellent in response to a determination that three times the standard deviation is less than or equal to the mean blood glucose level.

40. The system according to claim 26, wherein said instructions further cause the computing device to:

provide via the I/O device a report therapy goals have been achieved upon none of the conditions (i)-(iii) being met.

41. The system according to claim 26, wherein said instructions further cause the computing device to:

provide to a third party payer via the I/O device a report recommending a change in the treatment therapy in response to reporting the recommendation to change from the blood glucose treatment therapy of the multiple daily injections to a continuous subcutaneous insulin infusion (CSII) therapy.

42. The system according to claim 26, wherein the I/O device is one or more of a touch screen, a display, a speaker, and a printer.

* * * * *